(12) United States Patent
Larsen et al.

(10) Patent No.: US 7,460,234 B2
(45) Date of Patent: *Dec. 2, 2008

(54) LIGHT SCATTERING DETECTOR

(75) Inventors: David W. Larsen, St. Charles, MO (US); Zhi Xu, St. Louis, MO (US)

(73) Assignee: The Curators of the University of Missouri, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 11/853,682

(22) Filed: Sep. 11, 2007

(65) Prior Publication Data

US 2007/0296971 A1  Dec. 27, 2007

Related U.S. Application Data

(63) Continuation of application No. 10/780,278, filed on Feb. 17, 2004, now Pat. No. 7,268,881.

(51) Int. Cl.
*G01N 21/00* (2006.01)

(52) U.S. Cl. .................. 356/436; 356/432; 356/433; 356/435; 356/246

(58) Field of Classification Search ......... 356/432–444, 356/336–343, 37–41, 72–53, 244, 246; 250/574, 250/339.11, 227.22, 341.8, 222.2, 423 R
See application file for complete search history.

(56) References Cited

U.S. PATENT DOCUMENTS

| | | |
|---|---|---|
| 3,869,209 A | 3/1975 | Sigrist |
| 3,877,817 A | 4/1975 | Ralston |
| 4,053,229 A | 10/1977 | McCluney |
| 4,059,405 A | 11/1977 | Sodickson et al. |

(Continued)

FOREIGN PATENT DOCUMENTS

| | | |
|---|---|---|
| DE | 3841979 A1 | 12/1988 |
| JP | 6053919 | 2/1994 |

OTHER PUBLICATIONS

Haller, et al., "Double Beam Laser Absorption Spectroscopy: Shot Noise-Limited Performance at Baseband with a Novel Electronic Noise Canceller," SPIE, vol. 1435, Optical Methods for Ultrasensitive Detection and Analysis: Techniques and Applications, 1991, pp. 298-309.
Unknown, Product Catalog 2003, Ocean Optics, Inc.

*Primary Examiner*—Sang Nguyen
(74) *Attorney, Agent, or Firm*—Senniger Powers LLP

(57) ABSTRACT

The invention concerns high sensitivity light scattering detection and its application to evaporative light scattering detection in liquid chromatography. The exemplary embodiment includes a detection cell to accept particles suspended in a gas stream and permit a polarized light beam to pass through a trajectory of the particles and gas stream. A sample light detector is disposed to detect light scattered in the detection cell. A light trap accepts the polarized beam after it passes through the detection cell. The light trap includes an elongated housing through which the polarized beam passes, and light absorptive material within the elongated housing. An absorptive filter is aligned such that the angle of incidence of the light beam upon the filter approximates Brewster's angle and the electric field vector of the beam is aligned with the plane of incidence between the beam and the filter. Other embodiments of the invention provide increased light collection. Embodiments of the invention include temperature-controlled entrance and exit ports that control particle trajectory. Embodiments of the invention include a reference cell disposed between a detection cell and a light trap, and the reference cell includes lensing and a spherical mirror to direct light toward a reference light detector. The reference light detector provides a reference signal that may be used with noise cancellation circuitry, operating in either voltage or current mode, to reduce light source noise in the sample signal.

15 Claims, 9 Drawing Sheets

U.S. PATENT DOCUMENTS

| | | | |
|---|---|---|---|
| 4,070,111 | A | 1/1978 | Harrick |
| 4,178,103 | A | 12/1979 | Wallace |
| 4,213,703 | A | 7/1980 | Haunold et al. |
| 4,284,355 | A | 8/1981 | Hansen et al. |
| 4,343,552 | A | 8/1982 | Blades |
| 4,360,270 | A | 11/1982 | Jeck |
| 4,397,557 | A | 8/1983 | Herwig et al. |
| 4,518,700 | A | 5/1985 | Stephens |
| 4,565,447 | A | 1/1986 | Nelson |
| 4,725,140 | A | 2/1988 | Musha |
| 4,781,456 | A | 11/1988 | Nogami |
| 4,823,168 | A | 4/1989 | Kamahori et al. |
| 4,848,904 | A | 7/1989 | Sapp et al. |
| 4,922,309 | A | 5/1990 | Sekiwa et al. |
| 4,929,078 | A | 5/1990 | Harmon |
| 4,931,660 | A | 6/1990 | Mayer |
| 5,029,276 | A | 7/1991 | Buehler et al. |
| 5,061,065 | A | 10/1991 | Sommer |
| 5,134,276 | A | 7/1992 | Hobbs |
| 5,241,363 | A | 8/1993 | Garner |
| 5,301,007 | A * | 4/1994 | Ukon ............... 356/326 |
| 5,376,783 | A | 12/1994 | Vecht et al. |
| 5,434,412 | A | 7/1995 | Sodickson et al. |
| 5,452,085 | A | 9/1995 | Fancy et al. |
| 5,519,490 | A | 5/1996 | Nakata et al. |
| 5,540,825 | A | 7/1996 | Yeung et al. |
| 5,628,891 | A | 5/1997 | Lee |
| 5,680,209 | A | 10/1997 | Machler |
| 5,742,200 | A | 4/1998 | He |
| 5,745,243 | A | 4/1998 | Wilcox et al. |
| 5,745,293 | A | 4/1998 | Lassalle |
| 5,784,158 | A | 7/1998 | Stanco et al. |
| 5,872,361 | A | 2/1999 | Paoli et al. |
| 5,872,622 | A | 2/1999 | Schildmeyer et al. |
| 5,903,346 | A * | 5/1999 | Rinke et al. ............... 356/320 |
| 5,983,709 | A | 11/1999 | O'Keeffe |
| 6,002,477 | A | 12/1999 | Hammer |
| 6,040,914 | A | 3/2000 | Bortz et al. |
| 6,091,494 | A | 7/2000 | Kreikebaum |
| 6,097,034 | A | 8/2000 | Weckstrom et al. |
| 6,108,083 | A | 8/2000 | Machler |
| 6,184,537 | B1 | 2/2001 | Knox et al. |
| 6,207,369 | B1 | 3/2001 | Wohlstadter et al. |
| 6,243,170 | B1 | 6/2001 | Ershov |
| 6,249,348 | B1 | 6/2001 | Jung et al. |
| 6,297,505 | B1 | 10/2001 | Frandsen et al. |
| 6,414,754 | B1 | 7/2002 | Johnson |
| 6,449,040 | B1 | 9/2002 | Fujita |
| 6,490,530 | B1 | 12/2002 | Wyatt |
| 6,741,348 | B2 | 5/2004 | Larsen et al. |
| 6,903,818 | B2 | 6/2005 | Cerni et al. |
| 6,980,284 | B2 | 12/2005 | Ahn et al. |
| 2002/0021441 | A1 | 2/2002 | Norton et al. |
| 2003/0210465 | A1 | 11/2003 | Valenti |
| 2005/0012925 | A1 | 1/2005 | Saptari et al. |

* cited by examiner

LIGHT SCATTERING DETECTOR

FIELD OF THE INVENTION

A field of the invention is sample analysis. A specific exemplary field of the invention is liquid chromatography.

BACKGROUND

Sample analysis is used to determine a property or properties of a sample. One type of analysis is an optical analysis. Optical properties of a sample can provide information about the sample. Optical sample analysis is often used for detection in liquid chromatography. Liquid chromatography is used to separate a sample liquid mixture into its individual components and to quantify each component in the sample.

Evaporative light scattering detectors (ELSDs) are used for liquid chromatography analysis. In a typical liquid chromatography configuration, a solvent mixture (the mobile phase) containing dissolved solute (the analyte) flows continuously through a column and into an ELSD. Within the ELSD, liquid from the column is converted into small droplets by a nebulization process that uses a carrier gas, usually nitrogen. As the gas stream passes down a drift tube, the solvent evaporates and any non-volatile analyte present is ideally converted to finely dispersed solid particles that exit the drift tube and pass into the light scattering detector (LSD), which is the final section of the ELSD. When a sample is injected into an upstream end of the column, it travels slowly down the column and is separated into its individual components (the analytes). The analytes are sequentially eluted by the column. When an analyte is eluted, the liquid eluent contains analyte in addition to the mobile phase. At all other times, the liquid eluent is composed only of mobile phase.

A typical light scattering detector device (LSD) section of an ELSD is shown in FIG. 1. A light source 101 produces a collimated beam 102 that passes through apertures 103, which help to produce a well-defined beam. The light passes through a detector cell 104 and enters a light trap 105. The column eluent is converted into a gas stream, which exits a drift tube (not shown) and enters the detector cell 104 in a direction perpendicular to the plane of the paper in FIG. 1. Particles 106 within the gas stream pass through the beam 102, causing light to scatter. Some of the scattered light 107 is focused by a lens 108 onto a photodetector 109. The detector 109 is oriented to receive only scattered light; e.g., the detector axis 110 can be oriented perpendicular to beam 102, as shown in FIG. 1. The photocurrent of the detector 109 is processed by electronic circuitry (not shown) to provide the final output signal.

During operation of an ELSD equipped with an LSD such as that shown in FIG. 1, scattering from evaporated mobile phase liquids, from nebulizer carrier gas and from detector cell components produces a small signal in the detector 109, which is the background or baseline in the analysis. The light trap 105 is intended to capture the through-beam, the direct light 111 from the collimated beam 102, so that the through-beam does not reach the detector 109. If analyte particles are present, they also scatter light. Thus, analyte particles give an additional signal on top of the baseline. The total amount of light scattered by the analyte depends on both the number and size of the analyte particles that enter the light beam. A plot of detector signal versus time is called a chromatogram. A typical chromatogram exhibits multiple peaks, each corresponding to one of the eluted analytes.

A goal for ELSD units is to maximize sensitivity so the limit of detection is as low as possible. More powerful light sources and more efficient light collection optics can increase the size of the analyte signal, but the light source power is limited in commercial LSD sections because scattering from sources other than analyte particles quickly swamps the detector signal as the light source power is raised past relatively low light levels. Spurious scattering arises from sources other than the analyte particles including, for example, mobile phase components, nitrogen gas molecules, and the physical structure of the detector cell, as stated above. Conventional light traps also allow a small fraction of the light beam to be directed back toward the detector. These light traps are based on multiple reflections in which some fraction of the light is absorbed for each reflection. However, some degree of scattering also occurs during each reflection. Well-defined, e.g., collimated, light beams help reduce troublesome spurious scattering by detector cell components and the light trap at increased light source powers, but such beams may be difficult to realize with incandescent light sources.

Typically, the intensity of detected light attributable to particle scattering is only a tiny fraction (e.g., less than $10^{-8}$) of the original light beam intensity. Thus, even a very small amount of spurious scattering can produce a relatively intense background. This large background of scattered light results in a large, inconvenient DC baseline offset. The large background is also a source of noise and at high enough levels, it will saturate the detector.

SUMMARY OF THE INVENTION

An exemplary embodiment of the invention includes features for high sensitivity evaporative light scattering detection. The exemplary embodiment includes a detection cell to accept particles suspended in a gas stream and permit a polarized light beam to pass through a trajectory of the particles and gas stream. A light source produces the polarized beam. A sample light detector is disposed to detect light scattered in the detection cell. A light trap accepts the polarized beam after it passes through the detection cell. The light trap includes an elongated housing through which the polarized beam passes, and light absorbing material within the elongated housing. An absorptive absorptive filter properly aligned with the polarization direction of the beam is disposed to intersect the polarized beam. Additionally, a reference light detector may detect light passing the absorptive filter and provide a reference signal that may be used for noise cancellation.

Other embodiments of the invention provide increased light collection. An example embodiment uses a compound lens to efficiently direct light scattered from a light beam toward a sample detector and a spherical mirror to direct light toward the compound lens. Embodiments of the invention include temperature-controlled entrance and exit ports that control particle trajectory. Embodiments of the invention include a reference cell disposed between a detection cell and a light trap, and the reference cell includes lenses and a spherical mirror to direct light toward a reference light detector. The reference light detector provides a reference signal that may be used for noise cancellation. In another embodiment, a reference signal is provided by a reference light detector that detects light passing through an absorptive filter in the light trap.

DESCRIPTION OF THE EXEMPLARY EMBODIMENTS

Figure 1:
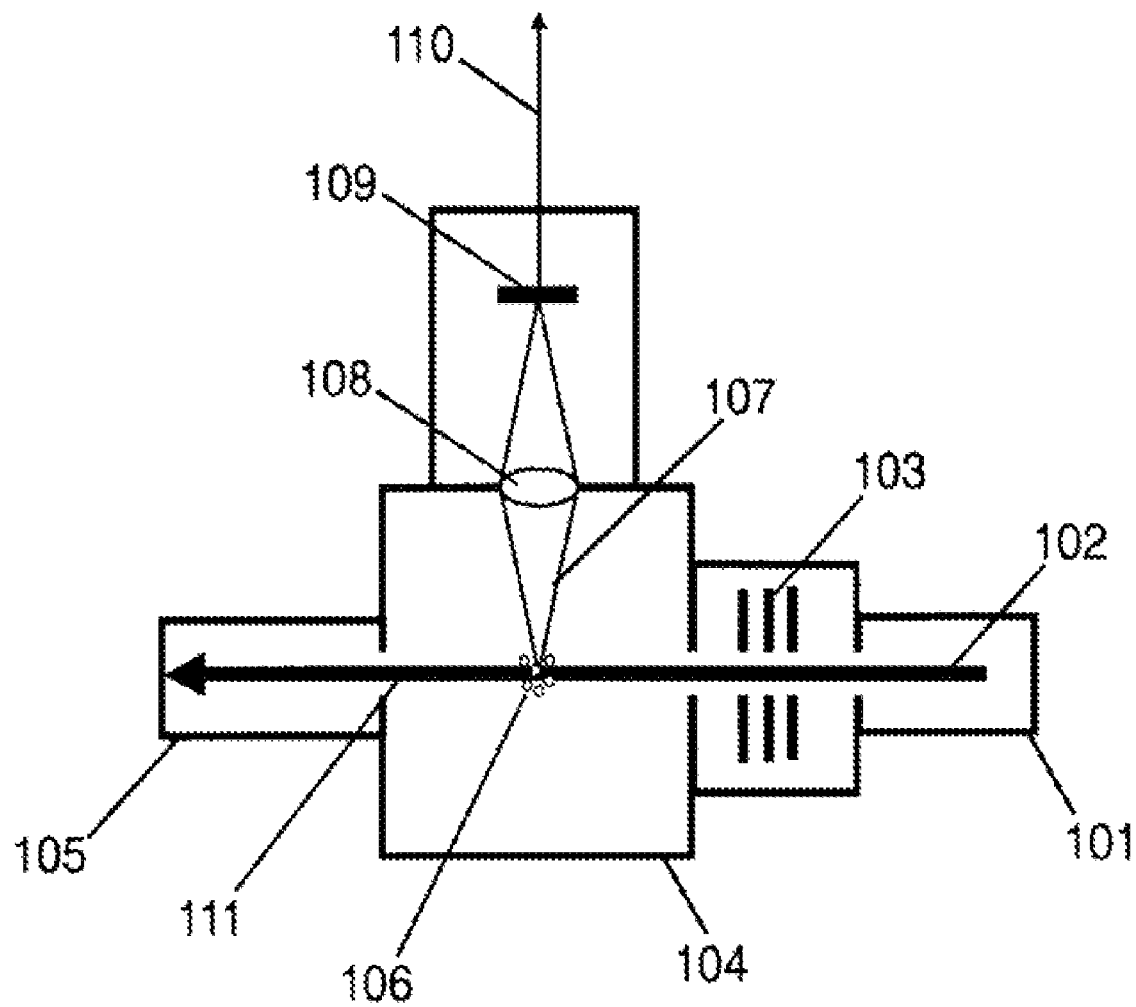
FIG. 1 is a block diagram illustrating a conventional light scattering detector.

The invention is directed to high sensitivity light scattering detection methods, devices and systems. Through various aspects of the invention, especially when applied in combination, scattering from background sources is made very low. A light scattering detector device of the invention accordingly has high sensitivity and exhibits a low limit of detection. A light scattering detector device of the invention may be an independent device, or it may form a section/component of another device, such as an evaporative light scattering detector device. Embodiments of the invention also obtain a reference signal from a through-beam portion (portion that is not scattered) of the light source that is detected at the backside of an absorptive filter at the end of a light trap. The reference signal is used in a detection circuit to cancel background effects, increase the sensitivity and lower the limit of detection.

In accordance with embodiments of the invention, a detection cell of a light scattering detector device includes a polarized light beam for producing scattering in the presence of analyte. Collection optics and a detector are disposed to detect a scattered portion of light as a sample signal. A light trap accepts a through-beam of the polarized light beam. The light trap is preferably an extended tube with a light-absorbing surface, e.g., a blackened surface. At an end of the extended tube is an absorptive filter. The absorptive filter has a high quality optical surface so that it reflects and/or scatters only a very small portion of the through-beam incident on its surface. A detector is on an opposite side of the absorptive filter and detects the small portion of the through-beam that is not absorbed by the filter. The small detected portion of the through-beam is used as a reference signal. A detection circuit permits subtraction of balanced reference and sample signals to cancel out the background level and to reduce noise attributable to fluctuations of light source power, which permits detection of very small scattering signals attributable to analyte scattering.

Embodiments of the invention achieve substantially improved sensitivity over that of current commercial units, as characterized by the signal to noise ratios demonstrated experimentally. A higher power light source may be used with the noise canceling features and detection methods of the invention. Embodiments of the invention may therefore significantly increase the amount of light scattered by the analyte and detected by the sample detector, i.e., the signal. Concurrent with analyte signal increase, there is also an increase in the noise level. This noise level is minimized by the invention, however, so that the increase in noise level is small relative to that of the signal, and there is an overall increase in the sensitivity (signal to noise ratio).

Exemplary embodiments will now be described with reference to the drawings. Schematic drawings will be understood by artisans, and are not to scale. Relative dimensions may also be exaggerated for purposes of illustration and understanding of the invention.

Exemplary embodiments include an LSD that is a modification of the FIG. 1 structure, in that the beam path, detector axis, and relative placement of the detection cell, light, source, and light trap is similar. These exemplary embodiments will be discussed with reference to some of the additional figures. A preferred device of the invention detects a through-beam portion of the collimated beam, which in the preferred device is a polarized beam. The through-beam portion may then be used for noise reduction in detection methods of the invention. The following brief mathematical analysis forms a foundation for increased sensitivity detection in an LSD device in accordance with exemplary embodiments of the invention. The analysis uses the following definitions:

P=light source power (W)

$F_{SX}$=fraction of light source power scattered by component X $F_{CX}$=fraction of light scattered by component X that reaches the detector S=photodetector sensitivity (A/W)

I=detector photocurrent=$P F_S F_C S$ (A)

Figure 2:
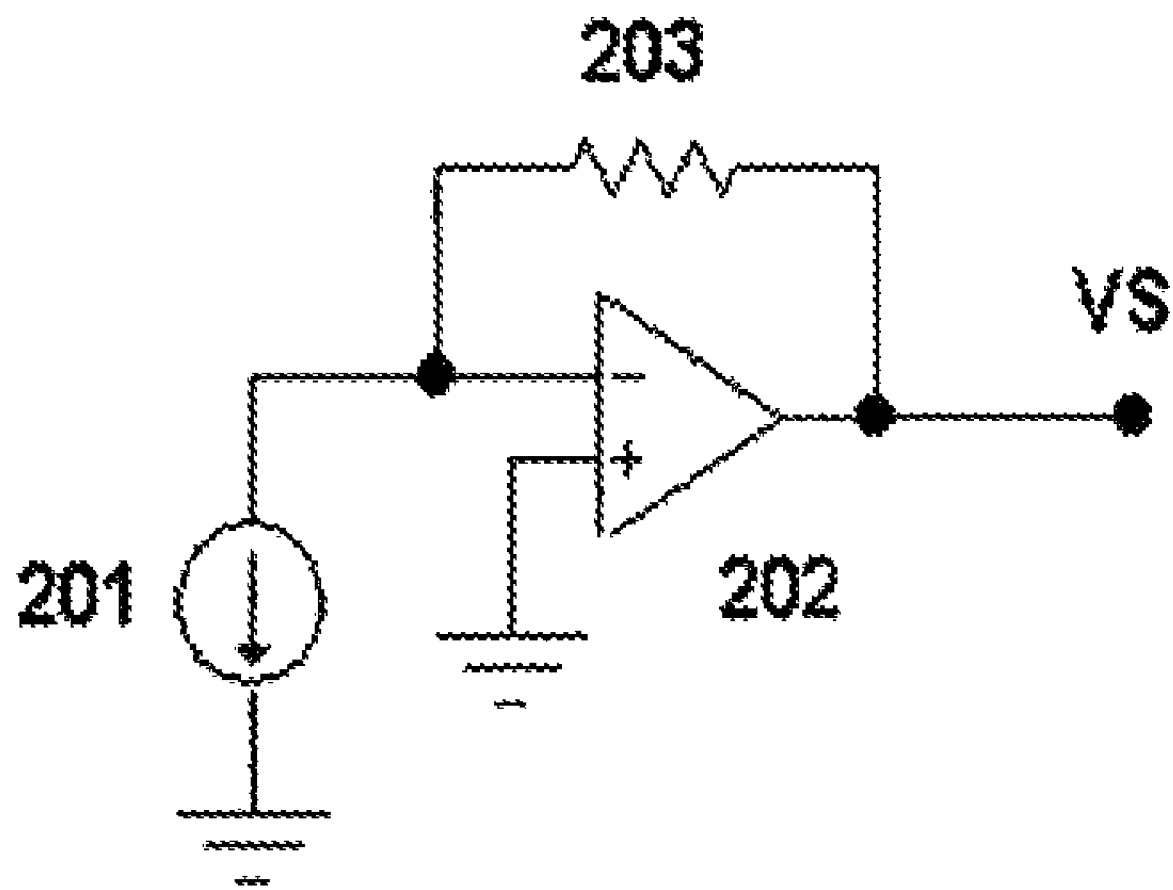
FIG. 2 shows an electronic circuit for converting a light detector photocurrent into a voltage.

FIG. 2 shows an electronic circuit used to analyze a signal obtained from a photodiode, represented as a current source 201. The photodiode detects light scattered in an LSD as the beam 102 (see FIG. 1) interacts with analyte particles from the gas stream. Ideally, the scattered light would be the only light to produce a signal in the photodiode. However, there are additional sources of light that are detected and add to the total signal. The photodiode produces a current that is input to an amplifier 202 with a feedback resistor 203. The photocurrent I is thus converted to an output sample detector voltage $V_S$, which is given by:

$$V_S = P\,S\,R(F_{SA}F_{CA} + F_{SB}F_{CB} + F_{SC}F_{CC}) \tag{1}$$

where $F_{SA}$, $F_{SB}$ and $F_{SC}$ are the fractions of light scattered by the analyte particles, the various gas molecules and the physical components of the detector cell 104, respectively, and $F_{CA}$, $F_{CB}$ and $F_{CC}$ are the fractions of collected light scattered by the analyte particles, the various gas molecules and the physical components of the detector cell 104, respectively.

With careful design, including high quality components, use of a collimated light beam and placement of apertures, scattering from detector cell components can be made very small so that the term $F_{SC} F_{CC}$ can be ignored. Thus, the output voltage $V_S$ contains a term for the analyte scattering and another for the background scattering from gas molecules, given by:

$$V_S = P\,F_{SA}\,F_{CA}\,S\,R + P\,F_{SB}\,F_{CB}\,S\,R \tag{2}$$

The first term is the analytical signal, i.e., the signal from the analyte particles, and the second term is the background.

The background term must be subtracted from $V_S$ to get the analytical signal $V_A$, which is given by:

$$V_A = V_S - P F_{SB} F_{CB} S R = P F_{SA} F_{CA} S R \quad (3)$$

From equation 3, the analyte signal $V_A$ can be calculated for any given set of component parameters. This enables a systematic investigation of the dependence of the signal on each parameter to be made and provides a method for optimizing the physical design of an LSD detector device.

In calculating $V_A$, it can be assumed that the fractions of scattered light, $F_{SA}$ and $F_{SB}$, are normally determined by factors not directly related to the LSD. The feedback resistance R is chosen based on the light intensities and the desired value of output voltages. Therefore $F_{SA}$, $F_{SB}$, and R can be considered to be fixed parameters with respect to the LSD. The photodetector sensitivity S is also a fixed parameter. This leaves P, $F_{CA}$ and $F_{CB}$, as the variable parameters.

From equation 3, it is seen that $V_A$ increases directly with P and $F_{CA}$. Thus, increasing the light source power and the efficiency of the collection optics will increase the analyte signal. However, the background level also increases with P and $F_{CB}$, and in addition, for the type of collection optics used in embodiments of the invention, $F_{CA}$ and $F_{CB}$ are approximately equal. Thus, the background level will also increase with increased light source power and collection optics efficiency. However, with a laser source and proper design, the background scattering $F_{SB}$ will be due essentially only to gas molecules, the density of which is fixed by the conditions of the analysis and not by design of the light scattering detector device. This means that $F_{SB}$ is effectively fixed and can be made relatively small.

The source noise level must also be considered, since it increases with high light source power and collection optics efficiency achieved in embodiments of the invention. The light source noise should be minimized by use of stable operating conditions for the light source (primarily with a good power supply and good thermal stability). As light source power increases, light source noise must eventually become dominant over all other sources of noise. Under this condition, source noise can be substantially reduced by use of an electronic noise cancellation method of the invention.

Noise terms mentioned above refer to random light source fluctuations with frequency components above about 0.1 Hz. Lower frequency noise components, often called drift, are also present. Thus, in addition to noise minimization, drift should also be minimized. Since drift is almost always thermal in nature, the temperature of the detector cell should be held as constant as possible.

Light emerging back out of the light trap also becomes important if there is significant light trap reflection and/or scattering when the power of the light source reaches a certain level. When light source power is relatively small, light emerging back out of the light trap may be ignored. In conventional ELSD devices, the failure to substantially reduce emergent light from the light trap is another impediment to raising the power of the light source. Preferred embodiments of the invention use a source power that is large enough to cause enough light to be reflected and/or scattered back out of a conventional light trap to cause severe noise, including large, unpredictable baseline shifts. This noise limits the attainable sensitivity of conventional devices. Embodiments of the invention use a light trap with high enough efficiency to permit use of a light source with power that would cause unacceptable noise with conventional light traps. Preferred embodiments use a high power polarized laser light source.

Commercial units have typically kept laser power below 5 mW to avoid the associated noise problems, but the invention permits use of lasers having much higher powers. Laser beam powers of 30 mW have been verified in prototypes, and embodiments with many hundreds and more mW are contemplated, with a primary limitation on laser powers being cost. Incoherent sources, such as incandescent sources, must be polarized and are comparably much higher power since only a small percentage of their power may be captured as a polarized beam. There is a cost associated with higher power lasers, and the cost is likely to be the primary upper limit on the laser power usable with embodiments of the invention until the cost of lasers, e.g., 200 mW and higher power lasers, decreases substantially. In a device constructed in accordance with inventive embodiments, an upper physical limit for laser power (aside from cost issues) may be set in accordance with the noise baseline (measurable and controllable in embodiments of the invention through the reference detection and noise cancellation) and DC offset. To optimize the light source power for a particular LSD device in accordance with one or more embodiments of the invention, light source power is increased until an unacceptable baseline noise measurement occurs or there is a high level of baseline noise with substantial DC offset. The optical components, and in particular the absorptive filter, used in embodiments of the invention may also place a limit on the power for the light source. For example, absorptive filters might only be able to handle a beam power of about 1 W.

Embodiments of the invention use a light trap matched to a well-defined polarized light source, e.g., a laser with polarized beam. Polarized light may also be obtained from an incandescent light source and a polarizer. Polarized light passing through an interface, e.g., from air into glass, has a well-defined behavior. With a polarized light beam, the fraction of incident light reflected from the interface depends on the angle of incidence and the orientation of the electric field vector with respect to the plane of incidence. Substantial alignment of the electric field vector and the plane of incidence defined by the polarized beam and the normal to the absorptive filter permits the fraction of reflected light to approach zero when the angle of incidence approximates Brewster's angle. It has been found that the electric field vector and the plane of incidence should align within 0-2°, and fraction of reflected light substantially increases for alignments in the 1-2° range compared to alignments below 1°. This forms a principle of the invention that allows a light trap to capture almost all of the polarized beam that it receives.

Figure 3:
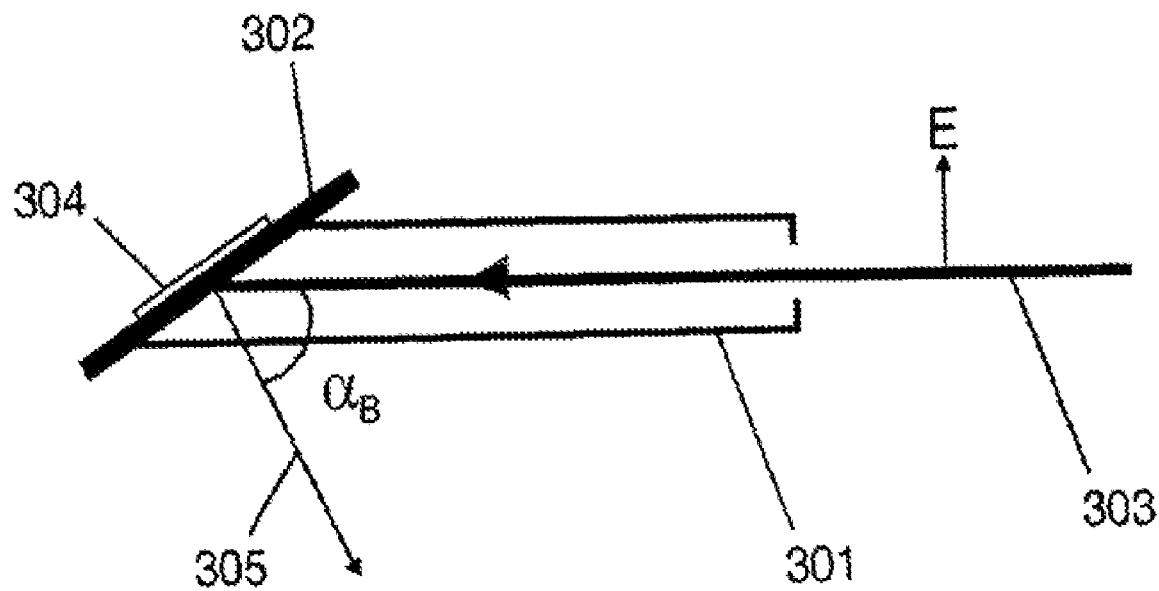
FIG. 3 is a block diagram illustrating a light trap of a light scattering detector device in accordance with a preferred embodiment of the invention.

FIG. 3 illustrates a preferred embodiment light trap, applied in a configuration as shown in FIG. 1, but where the light source 101 provides polarized light. The light trap of FIG. 3 includes an elongated housing 301, optically (and perhaps physically) open on one end, and having an absorptive filter 302 at an opposite end. The polarized through-beam 303 travels down the length of the tube toward the absorptive filter 302.

Generally, any type of absorptive filter may be used. The absorptive filter 302 in preferred embodiments is the neutral density type absorptive filter, and possesses a high optical surface quality, meaning that the amount of back scattering of polarized light from the filter surface will be extremely small. The neutral density filter preferably transmits very little light (e.g., $10^{-3}$ of the incident power, for an Optical Density=3). The absorptive neutral density filter has the advantage of absorbing light across a wide spectrum. The absorptive neutral density filter is especially effective, and particularly so when an incoherent light source is used to generate the polarized light beam (by passing an incoherent light source output through a polarizer). As an additional example of an absorptive filter, alternate embodiments of the invention use an absorptive band pass optical filter. The band pass optical filter must have a high quality optical surface and high absorptivity at the wavelength(s) of light used. The pass band is chosen to be well outside the band of the beam.

The beam then strikes the absorptive filter 302. The housing 301 may be formed of cylindrical tubing, the inside of which is coated with a material, e.g., blackened material, to absorb light. The orientation of the absorptive filter 302 is aligned such that the electric vector of the polarized light beam is in the plane of incidence as shown.

The angle of incidence of the beam 303 upon the absorptive filter 302 is at or near the so-called "Brewster's Angle," $\alpha_B$, which is defined as the angle between the incident ray 303 and the detector surface normal 305. $\alpha_B$ depends on the wavelength of the light and on the refractive index of the filter substrate. As an example, for 650 nm laser light and with filter refractive index of 1.51, $\alpha_B$ is about 56.4°. At Brewster's angle and for the orientation shown in FIG. 3, the reflectivity of the filter 302 surface approaches zero for polarized beam 303. As an example, for polarized light with the electric vector aligned in the plane of incidence, the fraction of reflected polarized light may be about $2\times10^{-5}$. The very small amounts of reflected and scattered light from the surface of the absorptive filter will be almost entirely absorbed by the inner surface of the housing 301.

Embodiments of the invention also provide a reference signal that may be employed to cancel background effects to increase sensitivity and lower the limit of detection. The very low transmission of the absorptive filter 302 (or a properly selected absorptive band pass filter) permits a photodetector 304 to detect light that passes through the absorptive filter. In a preferred embodiment, a silicon photodiode is mounted on a back surface of the absorptive filter 302. Even with the beam 303 having a high power as in preferred embodiments of the invention, light incident on the photodetector 304 is attenuated to a sufficient degree by the absorptive filter 302 to avoid detector saturation. For example, with a 10 mW laser and a $10^{-3}$ neutral density filter, about 100 nW will reach the photodetector 304 and this power can be easily monitored with the preferred embodiment detection circuit of FIG. 2, for example. The photodetector 304 serves as reference detector to monitor, preferably continuously, the power of the light beam. A reference signal is taken or derived from the photodetector and used, for example, in the preferred FIG. 5 circuit for noise cancellation.

The photodetector 304 receives, as described above, a very small portion of the power of the beam 303. Of this small amount of light, a fraction will be reflected off of the photodetector 304 surface back into the filter 302. However, that light will be further attenuated as it passes back through the filter for the second time.

The polarization ratio of a polarized laser beam 303 is typically 250:1 or better. This means that, in the FIG. 3 embodiment, there is a small percentage of light with polarization direction perpendicular to the plane of incidence at the air/filter interface. The reflectivity of the filter surface for this light component at Brewster's Angle is about 0.15. Therefore, reflection of this polarization component from the filter surface is about 0.06% of the total laser power. As with reflection of the primary polarization component in the plane of incidence, the reflected portion of the small secondary polarization component is almost completely absorbed by the blackened walls of the light trap housing 301. The net result is that the laser trap is highly efficient. This has been demonstrated in an experimental device constructed in accordance with FIG. 3 and having a neutral density filter with OD=3. For this device, less than $10^{-11}$ of the initial laser power reaches the sample detector 109 (see FIG. 1).

Figure 4:
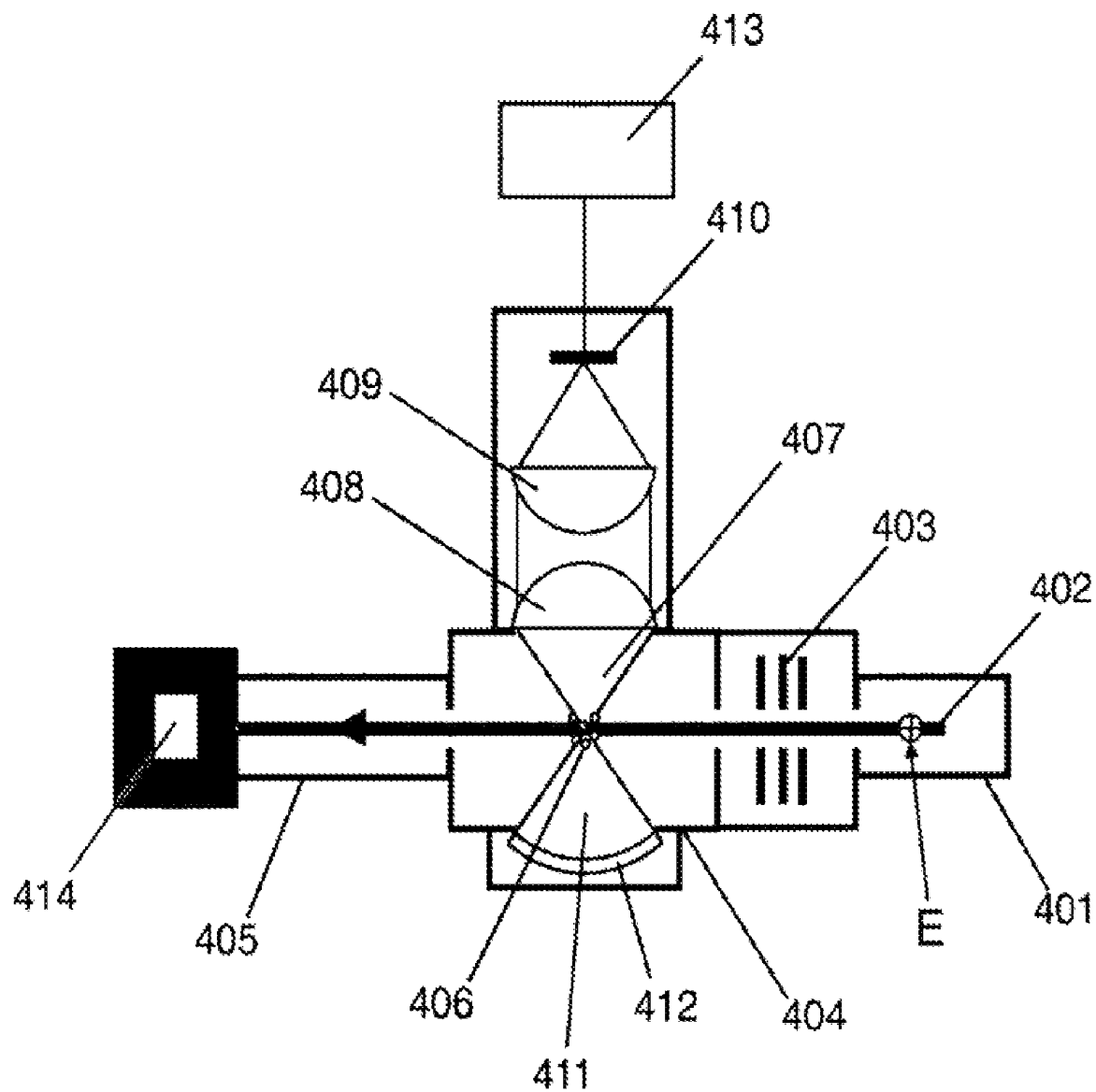
FIG. 4 is a block diagram illustrating a light scattering detector device with a single cell structure in accordance with a preferred embodiment of the invention.

FIG. 4 illustrates a preferred embodiment LSD. A laser 401 produces a polarized light beam 402 that travels through a set of apertures 403. The electric field E of the laser beam is polarized perpendicular to the plane of the paper in FIG. 4, as shown. The apertured beam passes into and through a detection cell 404. The beam path ends in a light trap 405 constructed in accordance with FIG. 3. Analyte particles 406 and gas molecules (typically nitrogen gas and vaporized solvent) enter the detection cell 404 from a drift tube (not shown) mounted with axis perpendicular to the plane of the paper and pass through part of the beam 402. The analyte particles 406 and gas molecules scatter a portion of the beam 402, and a portion 407 of the scattered light strikes a compound lens collector formed of two aspheric lenses 408 and 409 that efficiently collect light and focus it on a sample detector 410. Another portion 411 of the scattered light strikes a spherical mirror 412 that reflects the light back to its point of origin, so that it is also collected by the compound lens collector (lenses 408 and 409) and focused upon the sample detector 410. The spherical mirror 412 approximately doubles the amount of scattered light that is collected. The photocurrent from detector 410 is processed in electronic circuitry 413, e.g., the circuit in FIG. 2, to produce the final output signal.

A reference signal provided by the photodetector 414 (also 304 in FIG. 3) is a photocurrent that can be converted to a reference voltage $V_R$ by use of a circuit in accordance with FIG. 2. The reference voltage can be used for several purposes. It can be used as a diagnostic to assure proper laser power. It can be used to correct for laser drift by computing the ratio $V_S/V_R$ (see equation 1). This ratio is normalized with respect to laser power. It can be used with a noise cancellation circuit to greatly reduce or eliminate noise from the light source, which becomes particularly important in preferred embodiments of the invention where a high power light source is used.

Figure 5:
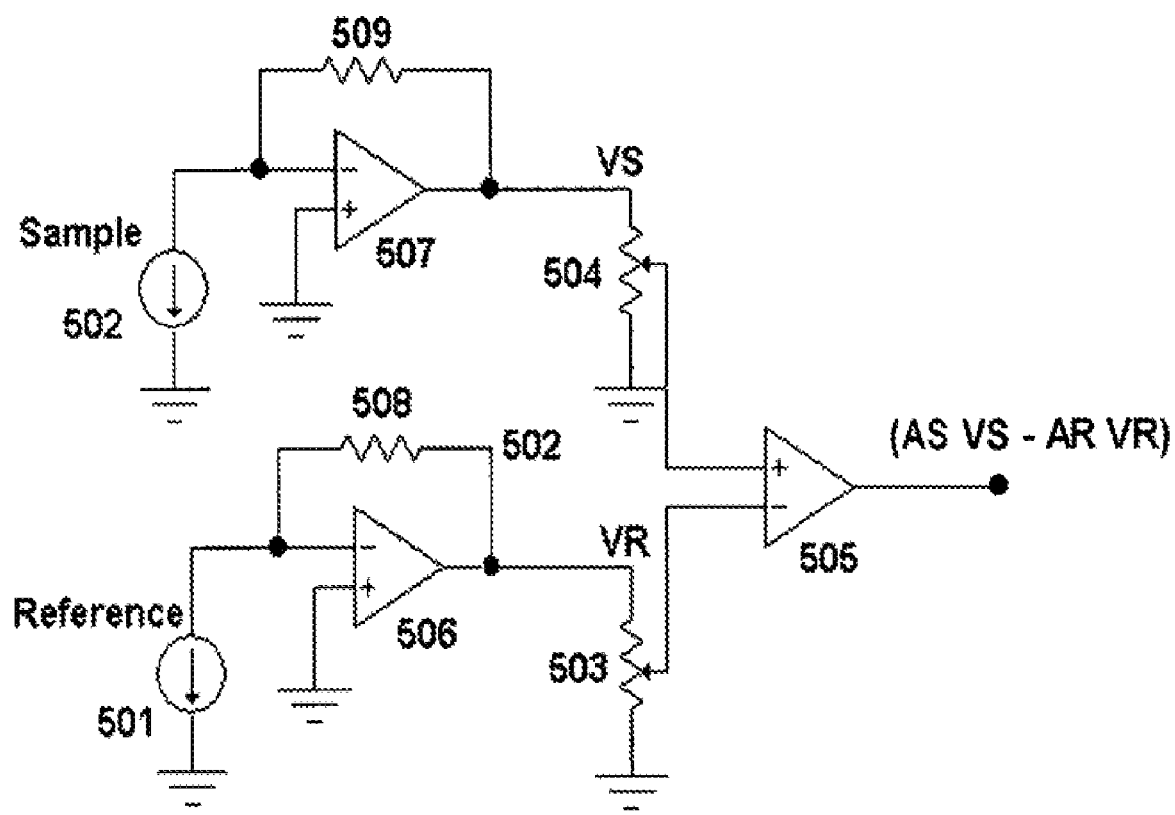
FIG. 5 shows a voltage mode noise cancellation circuit of a light scattering detector device in accordance with a preferred embodiment of the invention.

A preferred method for noise cancellation is effected by the preferred noise cancellation circuit shown in FIG. 5. The sample and reference photodetectors produce two voltages in FIG. 5, which will be referred to as sample and reference, $V_S$ and $V_R$, respectively. For large P and $F_C$ values, a large noise component is expected to arise from the light source fluctuation, which appears in a coherent manner at the two detectors. Thus, if a difference voltage $V_D = V_S - V_R$ is taken, the light source noise will tend to cancel. As the condition $V_S = V_R$ is approached, the light source noise will almost exactly cancel. For exact noise cancellation, amplifier offsets and detector dark currents must be taken into account. An added benefit obtained when $V_D$ is measured is that the large background offsets are eliminated.

Noise cancellation can be done in the voltage mode, as in FIG. 5. Photocurrents in the reference 501 and sample 502 photodetectors are converted to respective voltages, $V_R$ and $V_S$, which are variably attenuated by potentiometers 503 and 504 to produce voltages $A_S V_S$ and $A_R V_R$, where $A_S$ and $A_R$ are the potentiometer attenuation factors. The two voltages are then fed into a difference amplifier 505, the output of which is $A_S V_S - A_R V_R$. Adjustment of the potentiometers 503 and 504 permits the two input voltages to be equalized. Equalization produces a nulled output from the amplifier 505. In this output, the background is removed and source noise is cancelled.

For the detection of a small analyte signal, it is important to note that the background signal is very much larger than the analyte signal, so that when a small analyte signal appears, the output of amplifier 505 is only slightly offset and the noise cancellation efficiency is still very high. For detection of a large analyte signal, the noise cancellation efficiency is reduced, but since the analyte signal is large, noise cancellation is less important.

The reference 501 and sample 502 photodetectors, and the amplifiers 506 and 507 in FIG. 5 contribute Johnson noise as well as shot noise. However, since the magnitude of the reference photocurrent is determined by the optical density of the absorptive filter 302 (FIG. 3), it is possible to operate with a much higher photocurrent for the reference photodetector 501 than for the sample photodetector 502. Under these circumstances, a reference amplifier feedback resistor 508 should be much smaller than a sample amplifier feedback resistor 509, so that both shot noise and Johnson noise from the reference signal will be much less than that from the sample signal. Thus, the reference signal adds very little to the total noise.

The ratio $V_D/V_R$ can be used as the analytical signal, since light source noise and background offset will be removed by cancellation, and correction will be made for source power drift. Alternatively, if cancellation is not necessary, the ratio $V_S/V_R$, in which correction is made for source power drift, can be used as the analytical signal.

Figure 6:
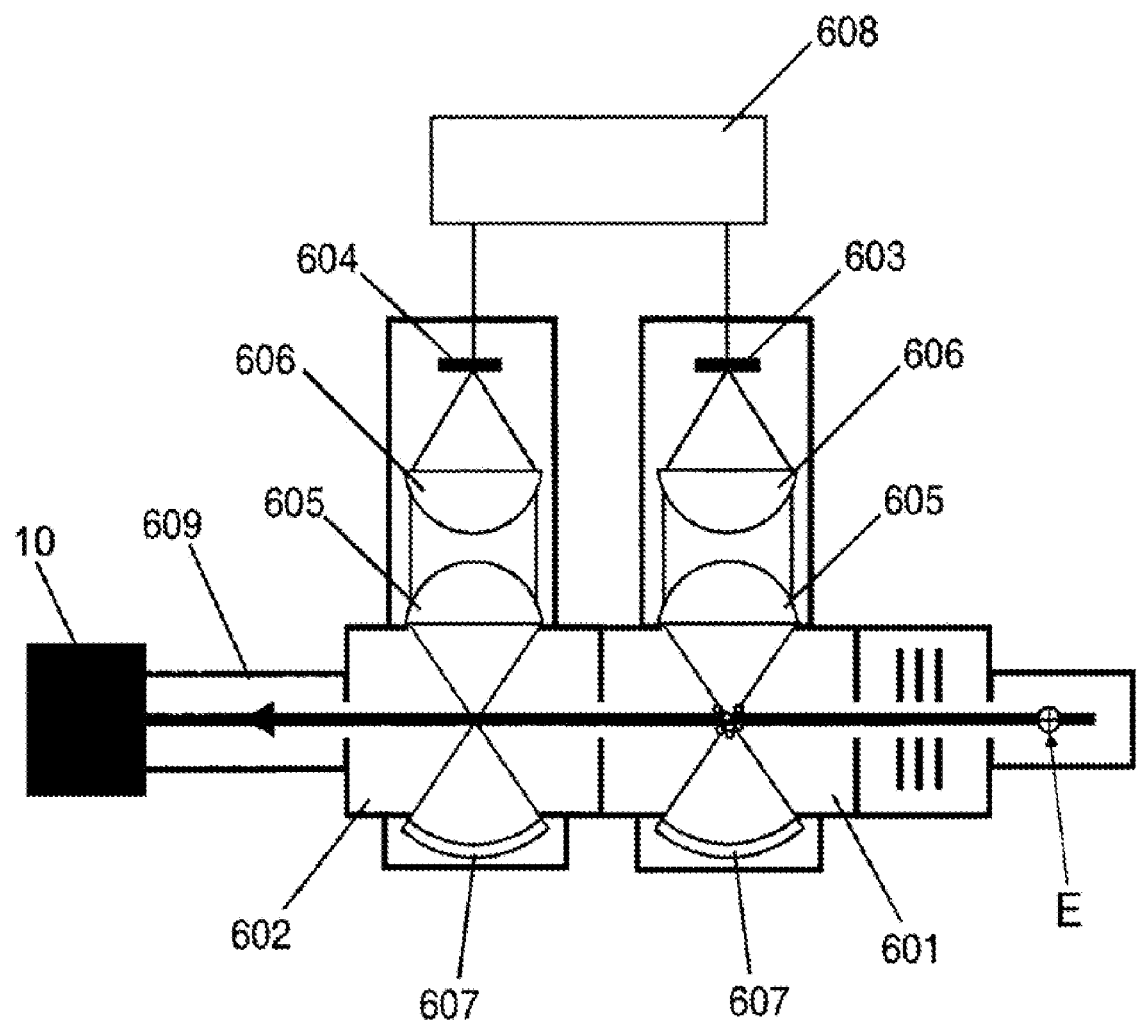
FIG. 6 is a block diagram illustrating a light scattering detector device with a two-cell structure in accordance with a preferred embodiment of the invention.

FIG. 6 illustrates a preferred embodiment LSD. Unlike the FIG. 4 arrangement, FIG. 6 has two cells, a sample cell 601 and a reference cell 602. Analyte and background scattering is present in the sample cell 601, while only background scattering is present in the reference cell 602. Scattered light is collected by identical optical components in both cells and focused on respective sample 603 and reference 604 detectors. Specifically, each of the sample and reference cells 601 and 602 includes aspheric lenses 605, 606 for collection optics, and a spherical mirror 607. Photocurrents from detectors 603 and 604 are processed in electronic circuitry 608 to produce the final output signal. A light trap 609 is formed in accordance with FIG. 3, without a reference photodetector since the reference photodetector 604 provides a signal for noise cancellation. An absorptive filter 610 is included as part of the light trap 609. With the two-cell configuration of FIG. 6, we have found experimentally that only scattered light from gas molecules and cell components reaches the reference detector, whereas scattered light from gas molecules, cell components and analyte particles reaches the sample detector. Thus, by use of a properly balanced cancellation circuit such as that shown in FIG. 5, it is possible to largely cancel the portion of the sample signal attributable to gas molecules and cell components, leaving primarily that due to analyte particles.

Figure 7:
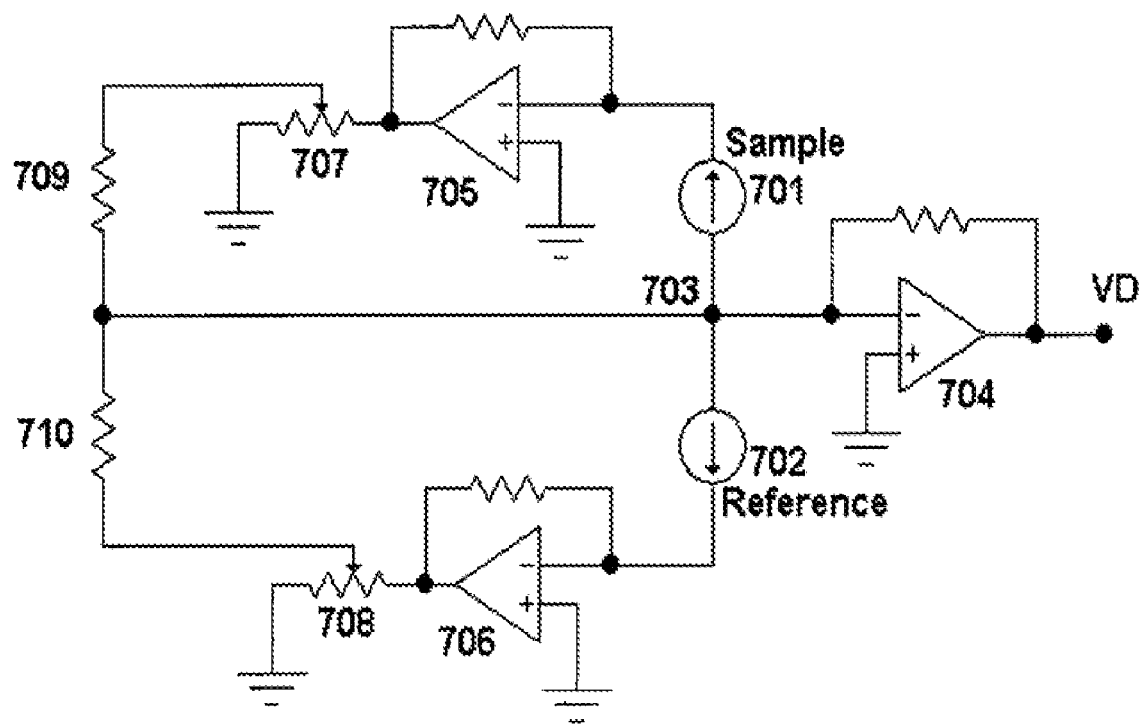
FIG. 7 shows a current mode noise cancellation circuit of a light scattering detector device in accordance with a preferred embodiment of the invention.

The FIG. 5 voltage mode noise cancellation circuit may also be used in the FIG. 6 LSD as described above. Another option is current mode noise cancellation. FIG. 7 presents an exemplary embodiment circuit that effects noise cancellation in the current mode. In FIG. 7, photocurrents from the sample 701 and reference 702 photodetectors are subtracted directly at a summing point 703 prior to conversion to an output voltage $V_D$ by amplifier 704. Photocurrent balance is achieved by using voltage outputs from auxiliary amplifiers 705 and 706. Potentiometers 707 and 708 are initially set to zero so that no current from the output of the auxiliary amplifiers 705 and 706 is fed to the summing point 703. The sign of the output voltage $V_D$ then permits determination of which photocurrent is larger, so that balance can be achieved by increasing the potentiometer setting for the detector with the smaller photocurrent. As that potentiometer setting increases, additional photocurrent is fed by the voltage appearing at that potentiometer (707 or 708) through its series resistor 709 or 710 into the summing point 703. This allows the photocurrents to be balanced. As mentioned above, for precise noise cancellation, amplifier offsets and detector dark currents must be taken into account. The two-cell LSD of FIG. 6 should produce similar photocurrents in the sample 701 and reference 702 photodetectors, which permits photocurrent balance to be achieved (for initialization with no analyte present) without drawing a large fraction of the total current from the auxiliary amplifiers 705 and 706. In a particular physical embodiment, if the two photocurrents are substantially different at initialization, it may be desirable to optically attenuate the scattering incident on the detector with the larger photocurrent to achieve balance. Initialization, as discussed above, can be simply achieved in commercial embodiments by an initialization process where an operator (through a switch or dial) adjusts the relevant potentiometer setting while reference and output analyte signals are monitored with no analyte present in the system. Computer-based, automatic initialization methods can also be implemented.

In the LSD embodiments of FIGS. 4 and 6, the lensing and reflections for detection of scattered light permits the photodetectors to see a small scattering region. The intensity of the scattered light signal obtained from the analyte particles depends on the number of particles that encounter the light beam in the scattering region. In ELSD devices, particles enter the detection cell through an inlet port on one side of the cell and exit the cell on an opposite side. Not all particles encounter the laser beam as they pass through the cell. This is because the width of the detection cell is much larger than the width the light beam, so that the particles will tend to spread as they travel through the detection chamber and some will effectively pass around the beam.

It is thus advantageous to make the path length through which the particles travel in the detection cell as short as possible and only slightly longer than the width of the light beam. This may be accomplished by extending the gas/particle entrance and exit ports well into the interior of the detection cell, preferably to near the point of beam and particle interaction. In such embodiments, entrance and exit ports guide particles in a trajectory to minimize spreading away from the laser beam. Furthermore, in order to avoid condensation of mobile phase components and analyte particles in the detection cell, the detection cell itself is normally heated. We have found that heating the cell causes slight positional shifts in optical components, lenses and mirrors, which lead to unwanted noise and drift. Such effects interfere with high sensitivity detection.

In preferred embodiments, including those constructed in accordance with the above discussed embodiments, the sample cell and reference cell are constructed out of thermally insulating material. This permits inlet and exit ports to be constructed out of thermally conducting material, such that the ports themselves may be directly heated to retard condensation, without heating the body of the cell. In other embodiments, a thermally conductive sample and or reference detection cell is used with thermally conductive and heated ports, but insulation is used to thermally isolate the ports and the cell body.

Figure 8:
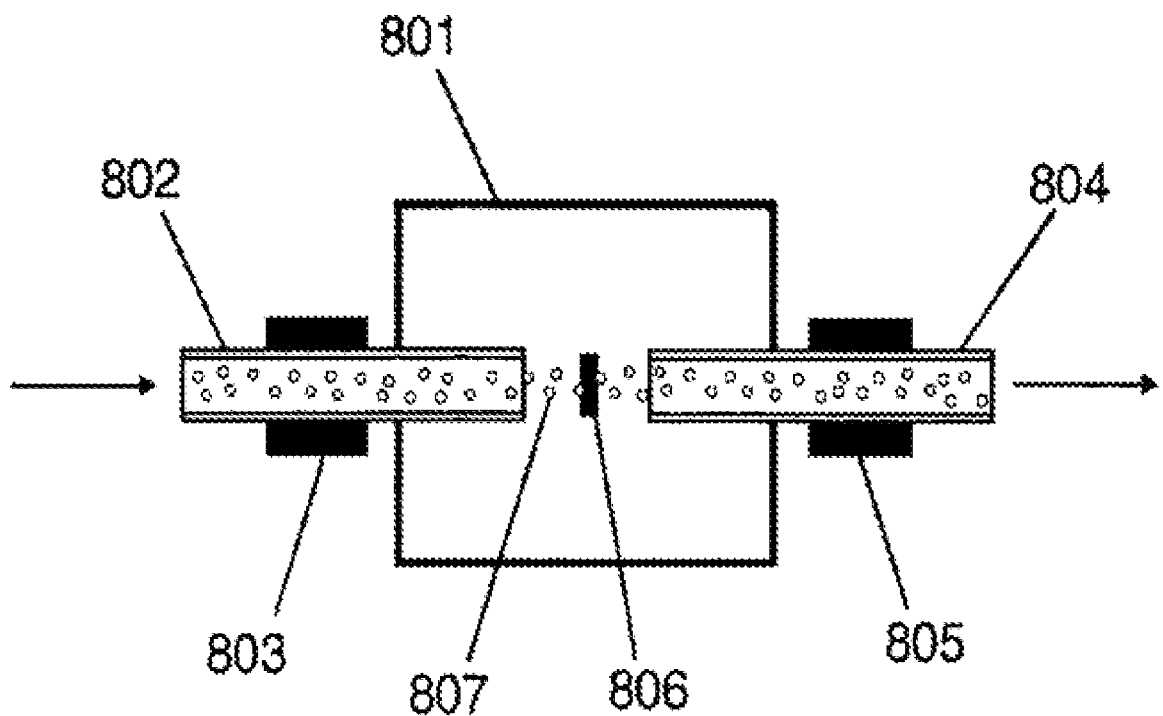
FIG. 8 is a schematic diagram of detection cell gas and particle entrance and exit port arrangement of a light scattering detector device in accordance with a preferred embodiment of the invention.

An exemplary embodiment is shown in FIG. 8, which illustrates a cross section of an LSD cell with heated inlet and exit ports for particle guidance. A detection cell 801 of the invention is fabricated from thermally insulating material, and the detection cell 801 includes an inlet port 802 heated by a heater 803, and an oppositely disposed exit port 804, heated by a heater 805. The heaters 803 and 805 may be used to raise the temperature of the ports without affecting the body of the cell 801 and the ports extend close to a beam path illustrated by a beam 806 in FIG. 8. The heaters 803 and 805 may be separate devices, or may be a common device with elements to heat each of the inlet port 802 and the exit port 804. Electrically resistive heaters, circulating fluid heaters, and other types of heaters may be used. Heaters that deliver localized heat to the inlet port 802 and the exit port 804 are well-suited to the invention.

Particles 807 are carried by the gas stream through the cell 801 entering from the inlet port 802 passing through the beam 806 and exiting via the exit port 804. Since the ports 802 and 804 are extended into the body of the detection cell 801 close to beam 806, particle spreading is minimized and a larger fraction of the particles encounters the beam. Experimental devices constructed in accordance with FIG. 8 have shown an increased analyte signal as compared to the detection cell without heated particle guidance, up to as much as a factor of two.

Laboratory devices have been constructed. Data concerning the devices is presented to illustrate, but not limit, levels achievable by application of various principles of the invention. It is expected that commercially manufactured devices applying the invention will exceed the performance of the experimental devices.

An experimental prototype was a two-cell unit, consistent with FIG. 6. Under the experimental conditions used, noise from the laser source was small relative to other sources of noise so that use of the noise cancellation circuitry was not necessary. Measurements were also made with a commercial ELSD unit, so that a sensitivity comparison could be made. Sensitivity is defined as the signal to noise ratio, $V_A/N_{OBS}$, where $V_A$ is taken to be the peak height (see equation 1) or the integrated area under the peak, and $N_{OBS}$ is the observed experimental noise.

Determination of Photometric Noise Levels: The simplest ELSD conditions for measurement of baseline noise are with only nitrogen flowing through the drift tube (e.g., at 2.0 L/min.) with a fixed drift tube temperature (e.g., 40° C.). The absence of a mobile phase assures that there is no noise originating from the nebulization and evaporation processes. Under these conditions, the measurements reflect the true photometric noise of the detection module used.

The photometric baseline was recorded for an Alltech Associates ELSD 2000, and the observed RMS noise was found to be 0.007 Scattering Units (SU). The SU designation is an arbitrary unit of convenient size.

The detector section from the Alltech Associates ELSD 2000 was removed, leaving the nebulizer, drift tube, and all other components untouched. The invention prototype LSD, according to FIG. 6, was then fitted to the Alltech unit and the measurement was repeated with the modified unit. Any difference in the results obtained in the two cases will thus be attributable to differences between the original Alltech LSD section and the invention prototype LSD.

The photometric baseline was again recorded, and in this case, it was necessary to continuously purge the cell with nitrogen gas to remove airborne dust particles, which cause extremely large, sharp noise spikes. The spikes were consistently positive-going from the baseline. Somewhat smaller, sharp noise spikes remained visible on the baseline even with nitrogen purging. The remaining noise spikes are attributable to small particles present in the nitrogen gas stream. The noise level of the baseline was calculated ignoring the noise spikes. The observed RMS noise level is 0.021 SU.

Thus, the photometric noise in the prototype is increased by a factor 0.021/0.007=3 over that of the commercial unit.

Determination of Analyte Signal Levels: A 20 μL sample of 10 ppm Hydrocortisone was run using the unmodified Alltech ELSD 2000 with 3.0 LPM nitrogen gas flow and 0.3 mL/min acetonitrile mobile phase. Three replicate injections gave the following results:

Average Peak Height=440 SU Average Peak Area=61.8 SU min.

The LSD section of the Alltech ELSD 2000 was again removed and the invention prototype LSD was fitted to the Alltech unit as described above. The measurements were repeated with the modified unit. The results were:

Average Peak Height=98,700 SU Average Peak Area=15,100 SU min.

From these data, the experimental increase in signal level is:

98,700/440=224 (based on Peak Height)

15,100/61.8=244 (based on Peak Area)

The signal to noise improvement thus ranges between 75 (Peak Height) and 81 (Peak Area).

Example of Low Level LC Detection: An Alltech ELSD equipped with the prototype LSD module was used to detect a sample that is considered below the ELSD detection limit. A 20 μL sample of 0.25 ppm Hydrocortisone was injected into a 2.1 mm×150 mm $C_{18}$ column with 0.1 mL/min flow rate of 45:55 (V:V) acetonitrile:water mobile phase.

Figure 9:
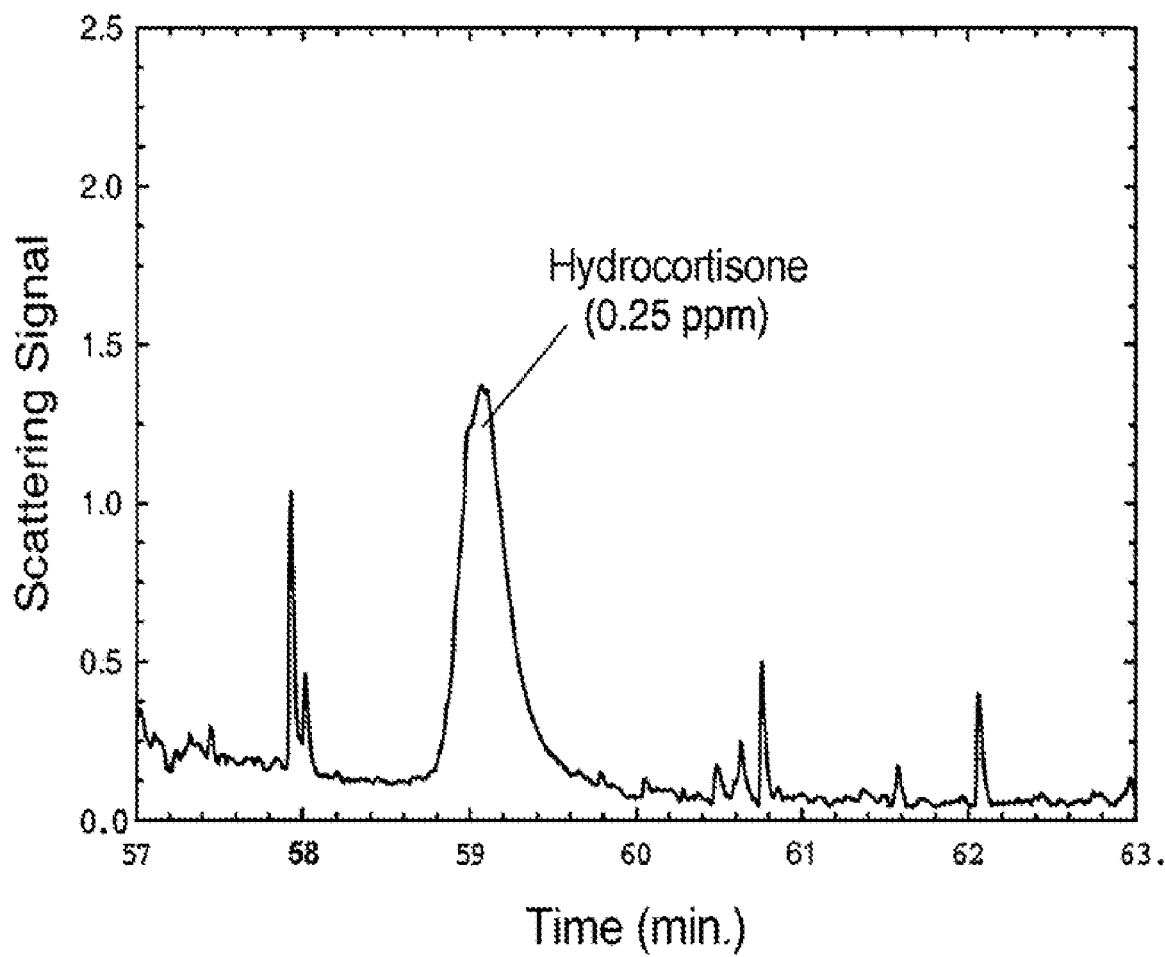
FIG. 9 is a chromatogram obtained with a prototype laboratory evaporative light scattering detector in accordance with embodiments of the invention.

The chromatogram is shown in FIG. 9 and the analyte peak can be clearly seen. The peak height is approx. 1.2 Scattering Units (SU). The peak is relatively broad due to the relatively low mobile phase flow rate. In order to obtain this chromatogram, it was necessary to carefully filter the mobile phase to remove all suspended particulates, which gave huge noise spikes, much greater than the height of the analyte peak. In addition, the nitrogen gas must also be carefully filtered. Despite the filtering, sharp positive-going noise spikes can still be seen. The heights of the particle noise spikes are comparable to that of the analyte peak, but the noise spikes are much more narrow, so they can be easily distinguished from the analyte peak. Incompletely vaporized mobile phase components also contribute baseline noise. The photometric noise of the LSD contributes almost nothing to the observed baseline noise level. The very small amount of baseline drift originates either in the chromatography column or in sections of the ELSD before the detection module.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A light scattering detector device, comprising:
    a detection cell to accept particles suspended in a gas stream and permit a polarized beam to pass through a trajectory of the particles and gas stream;
    a sample light detector disposed to detect light scattered in the detection cell;
    a sample compound lens collector to direct light scattered in the detection cell upon the sample light detector;
    a spherical mirror to direct light scattered in the detection cell to the compound lens collector;
    a light trap that accepts the polarized beam after it passes through the detection cell, the light trap including, an elongated housing through which the polarized beam passes, and light absorptive material within the elongated housing; and an absorptive filter disposed to substantially align the electric field vector of the polarized beam with the plane of incidence defined by the polarized beam and the normal to said absorptive filter, and disposed to intersect the polarized beam at an angle of incidence that approximates Brewster's angle;

a reference cell through which the polarized beam passes before the polarized beam is accepted by said light trap;

a reference light detector;

a reference cell compound lens collector to direct light scattered in the reference cell upon the reference light detector; and a spherical mirror to direct light scattered in the reference cell to the reference cell compound lens collector.

2. The device of claim 1, further comprising a light source to produce the polarized beam;
wherein the light source comprises a polarized laser having a power of at least 5 mW.

3. The device of claim 1, further comprising a light source to produce the polarized beam;
wherein the light source comprises an incoherent source with a polarizer.

4. The device of claim 1, wherein said sample compound lens collector comprises two aspheric lenses.

5. The device of claim 1, further comprising a light source to produce the polarized beam; and
a set of apertures disposed between said light source and said detection cell.

6. The device of claim 1, further comprising:
an inlet port that extends into said detection cell to control the trajectory of the particles and gas stream; and
an exit port that extends into said detection cell to control the trajectory of the particles and gas stream.

7. The device of claim 1, further comprising:
an inlet port that extends into said detection cell to control the trajectory of the particles and gas stream; and
an exit port that extends into said detection cell to control the trajectory of the particles and gas stream.

8. The device of claim 7, further comprising means to heat said inlet port and said exit port, wherein said detection cell is thermally isolated from said exit port and said inlet port.

9. The device of claim 8, wherein said detection cell is thermally nonconductive so that it is thermally isolated from said exit port and said inlet port.

10. The device of claim 8, wherein said detection cell is insulated from said exit port and said inlet port so that it is thermally isolated from said exit port and said inlet port.

11. The device of claim 1, wherein said absorptive filter comprises an absorptive neutral density filter.

12. The device of claim 1, wherein said absorptive filter comprises an absorptive band pass filter having a pass band set to mismatch the band of the polarized beam.

13. The device of claim 1, wherein the electric field vector and the plane of incidence defined by the polarized beam and the normal to said absorptive filter align within 2° or less.

14. The device of claim 13, wherein the electric field vector and the plane of incidence defined by the polarized beam and the normal to said absorptive filter align within 1° or less.

15. A light scattering detector device, comprising:
a detection cell to accept particles suspended in a gas stream and permit a polarized beam to pass through a trajectory of the particles and gas stream;
a sample light detector disposed to detect light scattered in the detection cell;
a sample compound lens collector to direct light scattered in the detection cell upon the sample light detector;
a light trap that accepts the polarized beam after it passes through the detection cell, the light trap including,
an elongated housing through which the polarized beam passes, and light absorptive material within the elongated housing; and
an absorptive filter disposed to substantially align the electric field vector of the polarized beam with the plane of incidence defined by the polarized beam and the normal to said absorptive filter, and disposed to intersect the polarized beam at an angle of incidence that approximates Brewster's angle;
a reference cell through which the polarized beam passes before the polarized beam is accepted by said light trap;
a reference light detector; and
a reference cell compound lens collector to direct light scattered in the reference cell upon the reference light detector.

* * * * *